US006770766B2

(12) United States Patent
Geller et al.

(10) Patent No.: US 6,770,766 B2
(45) Date of Patent: Aug. 3, 2004

(54) POLYAMINO ACID-CATALYZED PROCESS FOR THE ENANTIOSELECTIVE EPOIXDATION OF α,β-UNSATURATED ENONES AND α,β-UNSATURATED SULFONES

(75) Inventors: Thomas Geller, Odenthal (DE); Christa Maria Krüger, Münster (DE); Hans-Christian Militzer, Odenthal (DE)

(73) Assignee: Bayer Chemicals AG, Leverkusen (DE)

( * ) Notice: Subject to any disclaimer, the term of this patent is extended or adjusted under 35 U.S.C. 154(b) by 0 days.

(21) Appl. No.: 10/202,255

(22) Filed: Jul. 24, 2002

(65) Prior Publication Data

US 2003/0087401 A1 May 8, 2003

(30) Foreign Application Priority Data

Jul. 27, 2001 (DE) .......................................... 101 36 131

(51) Int. Cl.[7] .................... C07D 301/12; C07D 301/14; C07D 301/19
(52) U.S. Cl. ....................... 549/531; 549/524; 549/525; 549/529
(58) Field of Search ................................ 549/531, 524, 549/525, 529

(56) References Cited

U.S. PATENT DOCUMENTS

| 6,225,482 B1 | 5/2001 | Drauz et al. ................. 549/525 |
| 6,409,769 B1 | 6/2002 | Shi ............................ 549/519 |
| 2002/0133031 A1 | 9/2002 | Shi ............................ 549/524 |

FOREIGN PATENT DOCUMENTS

| EP | 0 403 252 | 12/1990 |
| EP | 1 006 111 | 6/2000 |
| WO | 96/33183 | 10/1996 |

OTHER PUBLICATIONS

Bioorganic & Medical Chemistry, 7, 1999, pp. 2145–2156, "Polyamino Acids as Catalysts in Asymmetric Synthesis" by M. J. Porter, S. M. Roberts, and J. Skidmore.
Tetrahedron Letters, 40, 1999, pp. 5421–5424, "PaaSicats: Powerful Catalysts for Asymmetric Epoxidation of Enones. Novel Syntheses of α-Arylpropanoic Acids including (S)-Fenoprofen" by L. Carde, H. Davies, T. P. Geller and S. M. Roberts.
Tetrahedron Letters, 39, 1998, pp. 7353–7356, "Water vs. Desiccant. Improvement of Yb–BINOL Complex Catalyzed Enantioselective Epoxidation of Enones" by S. Watanabe, Y. Kobayashi, T. Arai, H. Sasai, M. Bougauchi, and M. Shibasaki.
Tetrahedron Letters, 39, 1998, pp. 1599–1602, "Asymmetric Phase–Transfer Mediated Epoxidation of α, β–Unsaturated Ketones Using Catalysts Derived From *Cinchona* Alkaloids" by B. Lygo and P. G. Wainwright.

Tetrahedron Letters, No. 21, pp. 1831–1834, 1976, "Catalytic Asymmetric Induction in Oxidation Reactions. The Synthesis of Optically Active Epoxides." by R. Helder, J. C. Hummelen, R. W. P. M. Laane, J. S. Wiering and H. Wynberg.
Tetrahedron Letters, 39, 1998, pp. 7563–7566, "Asymmetric Epoxidation of α,β–Unsaturated Ketones Under Phase–Transfer Catalyzed Conditions" by S. Arai, H. Tsuge and T. Shioiri.
Tetrahedron Letters, 39, 1998, pp. 7321–7322, "Remarkable Ligand Effect on the Enantioselectivity of the Chiral Lanthanum Complex–Catalyzed Asymmetric Epoxidation of Enones" by K. Daikai, M. Kamaura, and J. Inanaga.
Angew. Chem. Int. Ed. Engl., 1997, 36, No. 4, pp. 410–412, "Asymmetric Epoxidation of Chalcones with Chirally Modified Lithium and Magnesium tert–Butyl Peroxides" by C. L. Eiston, R. F. W. Jackson, S. J. F. MacDonald and P. J. Murray.
Liebigs Ann./Recueil, 1997, pp. 1101–1113, "Zinc–Mediated Asymmetric Epoxidation of α–Enones" by D. Enders, J. Zhu, and L. Kramps.
Tetrahedron Letters 40, 1999, pp. 5207–5210, "cis–Selective Aziridination of cis– or trans–α, β–Unsaturated Amides Using Diaziridine" by K. Hori, H. Sugihara, Y. N. Ito and T. Katsuki.
J. Chem. Soc., Perkin Trans. I, 1982, pp. 1317–1324, "Synthetic Enzymes. Part 2.[1] Catalytic Asymmetric Epoxidation by means of Polyamino–acids in a Triphase System" by S. Juliá, J. Guixer, J. Masana and J. Rocas.
Org. Synth. Mod. Trends. Proc. 1UPAC Symp., 6th, 1986, pp. 275–284, "Asymmetric syntheses catalyzed by natural and synthetic peptides" by S. Colonna, A. Manfredi and M. Spadoni.
J. Chem. Soc. Perkin Trans. 1, 1995, pp. 1467–1468, "Enantiocomplementary asymmetric epoxidation of selected enones using poly–L–leucine and poly–D–leucine" by M. E. L. Sánchez and S. M. Roberts.
J. Chem. Soc., Perkin Trans. 1, 1997, pp. 3501–3507, "Improved procedure for Juliá–Colonna asymmetric epoxidation of α,β–unsaturated ketones: total synthesis of diltiazem and Taxol™ side–chain" by B. M. Adger et al.
Tetrahedron Letters, 42, 2001, pp. 3741–3743, "Asymmetric epoxidation of a geminally–disubstituted and some trisubstituted enones catalysed by poly–L–leucine" by P. A. Bentley, J. F. Bickley, S. M. Roberts and A. Steiner.

(List continued on next page.)

*Primary Examiner*—Ba K. Trinh
(74) *Attorney, Agent, or Firm*—Godfried R. Akorli; Diderico van Eyl

(57) ABSTRACT

The invention relates to a novel process that makes it possible to epoxidize α,β-unsaturated enones or α,β-unsaturated sulfones with high conversions and enantiomeric excesses in the presence of a water-soluble base, an oxidant, a diastereomer- and enantiomer-enriched homopolyamino acid as catalyst, water, an organic solvent that is immiscible or has only limited miscibility with water, and a specific phase-transfer catalyst as cocatalyst.

21 Claims, No Drawings

OTHER PUBLICATIONS

Chem. Commun., 1997, pp. 739–740, "Asymmetric epoxidation of enones employing polymeric α–amino acids in non–aqueous media" by P. A. Bentley et al.

Chirality 9: pp. 198–202, 1997, "Preparation of Polyamino Acid Catalysts for Use in Juliá Asymmetric Epoxidation" by P.A. Bentley et al.

Chem. Commun., 1998, pp. 1159–1160, "New procedures for the Juliá–Colonna asymmetric epoxidation: synthesis of (+)–clausenamide" by M. W. Cappi et al.

Tetrahedron: Asymmetry, vol. 8, No. 19, pp. 3163–3173, 1997, "Synthetic applications of polymeric α–amino acids" by S. Ebrahim and M. Wills.

J. Org. Chem., 1993, 58, pp. 6247–6254, "A Practical Enantioselective Synthesis of SK&F 104353" by J. R. Flisak et al.

Angew. Chem. Int. Ed. Engl. 19, 1980, No. 11, "Synthetic Enzymes". Highly Stereoselective Epoxidation of Chalcone in a Triphasic Toluene–Water–Poly[(S)–alanine] System by S. Juliá, J. Masana, and J. C. Vega.

Tetrahedron Letters, 39, 1998, pp. 9297–9300, "Towards a Mechanistic Insight into the Juliá–Colonna Asymmetric Epoxidation of α,β–Unsaturated Ketones Using Discrete Lengths of Poly–leucine." by P. A. Bentley et al.

Baures P. W. et al: "An efficient asymmetric synthesis of substituted phenyl glycidic esters" Tetrahedron Letters., Bd. 31, Nr. 45, 1990, Seiten 6501–6504, XP002006755, Elsevier Science Publishers, Armsterdam., NL ISSN: 0040–4039 das ganze Dokument.

Dhanda, Anupma et al: "PaaSiCats: Novel polyamino acid catalysts" Chirality (2000), 12(5/6), 313–317, XP008009815, das ganze Dokument.

Flood R. W. et al: "Efficient asymmetric epoxidation of alpha, beta–unsaturated ketones using a soluble triblock polyethyleneglycol–polyamino acid catalyst" Organic Letters., Bd. 3, Nr. 5, 8. Marz 2001 (Mar. 8, 2001), Seiten 683–686, XP002219131 ACS, Washington, DC., US ISSN: 1523–7060 das ganze Dokument.

POLYAMINO ACID-CATALYZED PROCESS FOR THE ENANTIOSELECTIVE EPOIXDATION OF α,β-UNSATURATED ENONES AND α,β-UNSATURATED SULFONES

BACKGROUND OF THE INVENTION

The invention relates to a novel polyamino acid-catalyzed process for the enantioselective epoxidation of α,β-unsaturated enones and α,β-unsaturated sulfones in the presence of specific cocatalysts.

Chiral, nonracemic epoxides are known as valuable synthons for preparing optically active drugs and materials (for example, (a) *Bioorg. Med. Chem.*, 1999, 7, 2145–2156; and (b) *Tetrahedron Lett.*, 1999, 40, 5421–5424). These epoxides can be prepared by enantioselective epoxidation of double bonds. In this case, two stereocenters are produced in one synthetic step. It is therefore not surprising that a large number of methods have been developed for the enantioselective epoxidation of double bonds. However, there is still a great need for novel, improved methods for enantioselective epoxidation.

The epoxidation methods limited to the specific substrates in each case include methods for the enantioselective epoxidation of α,β-unsaturated enones.

Thus, for example, the use of chiral, nonracemic alkaloid-based phase-transfer catalysts for the epoxidation of enones is described in *Tetrahedron Lett.*, 1998, 39, 7563–7566, *Tetrahedron Lett.*, 1998, 39, 1599–1602, and *Tetrahedron Lett.*, 1976, 21, 1831–1834.

*Tetrahedron Lett.*, 1998, 39, 7353–7356, *Tetrahedron Lett.*, 1998, 39, 7321–7322, and *Angew. Chem., Int. Ed. Engl.*, 1997, 36, 410–412 furthermore describe possibilities for the metal-catalyzed asymmetric epoxidation of enones using organic hydroperoxides.

WO-A 99/52886 describes the possibility of enantioselective epoxidation of enones in the presence of catalysts based on sugars.

Another method for epoxidation using Zn organyls and oxygen in the presence of an ephedrine derivative has been published in *Liebigs Ann./Recueil*, 1997, 1101–1113.

*Angew. Chem., Int. Ed. Engl.*, 1980, 19, 929–930, *Tetrahedron*, 1984, 40, 5207–5211, and *J. Chem. Soc., Perkin Trans.* 1, 1982, 1317–24 describe the Juliá epoxidation method in which enantiomer- and diastereomer-enriched polyamino acids are able, in the presence of aqueous hydrogen peroxide and NaOH solution and of an aromatic or halogenated hydrocarbon as solvent, to catalyze the enantioselective epoxidation of α,β-unsaturated enones. Further developments of these so-called three-phase conditions are to be found in *Org. Synth.; Mod. Trends, Proc. IUPAC Symp. 6th.*, 1986, 275. The method is now generally referred to as the Juliá-Colonna epoxidation.

According to EP-A 403,252, it is possible also to employ aliphatic hydrocarbons advantageously in this Juliá-Colonna epoxidation in place of the original solvents.

WO-A 96/33183 describes as a specific embodiment the possibility of carrying out the enantioselective epoxidation of enones also in the presence of the phase-transfer catalyst Aliquat® 336 ($[(CH_3)(C_8H_{17})_3N^+]Cl^-$) if at the same time a polyamino acid, an organic solvent (such as, for example, dichloromethane), sodium perborate (which is of low solubility in water) as oxidant, and alkali (for example, NaOH) are present.

Despite these improvements, the three-phase conditions have distinct disadvantages. The reaction times under the original conditions are in the region of days even for reactive substrates. For example, 1 to 6 days are required for the epoxidation of trans-chalcone, depending on the polyamino acid used (*Tetrahedron*, 1984, 40, 5207–5211). A preactivation of the polyamino acid carried out in the reaction vessel, by stirring in the solvent with the addition of NaOH solution for 12 to 48 h, shortens the reaction time for many substrates to 1 to 3 days. In this case, no intermediate workup of the catalyst is necessary (EP-A 403,252). The preactivation can be reduced to a minimum of 6 h in the presence of the NaOH/hydrogen peroxide system (*J. Chem. Soc., Perkin Trans.* 1, 1995, 1467–1468).

Despite this improvement, the three-phase method cannot be applied to substrates which are sensitive to hydroxide ions (*J. Chem. Soc., Perkin Trans.* 1, 1997, 3501–3507). A further disadvantage of these classical conditions is that the polyamino acid forms a gel during the reaction (or even during the preactivation). This restricts the required mixing during the reaction and impedes the working up of the reaction mixture.

*Tetrahedron Lett.*, 2001, 42, 3741–43 discloses that under the three-phase conditions the addition of the phase-transfer catalyst Aliquat® 336 in the epodixation of phenyl-E-styryl sulfone leads to only a slow reaction rate (reaction time: 4 days) and a poor enantiomeric excess (21% ee). To date, no example of the use of phase-transfer catalysts (PTC) for the epoxidation of α,β-unsaturated enones under the classical three-phase Juliá-Colonna conditions has been disclosed.

The Juliá-Colonna epoxidation has been improved further by a change in the reaction procedure. According to *Chem. Commun.*, 1997, 739–740, (pseudo)-anhydrous reaction conditions can be implemented by using THF, 1,2 dimethoxyethane, tert-butyl methyl ether, or ethyl acetate as solvent, a non-nucleophilic base (for example, DBU), and a urea/hydrogen peroxide complex as oxidant. The epoxidation takes place distinctly more quickly under these so-called two-phase reaction conditions. According to *J. Chem. Soc., Perkin Trans.* 1, 1997, 3501–3507, therefore, the enantioselective epoxidation of hydroxide-sensitive enones under the Juliá-Colonna conditions is also possible for the first time in this way.

However, the observation that, on use of the two-phase conditions, the polyamino acid must be preactivated in a separate process in order to achieve rapid reaction times and high enantiomeric excesses proves to be a distinct disadvantage. Several days are needed for this preactivation, which takes place by stirring in a toluene/NaOH solution. According to *Tetrahedron Lett.*, 1998, 39, 9297–9300, the required preactivated catalyst is then obtained after a washing and drying procedure. However, the polyamino acid preactivated in this way forms a paste under the two-phase conditions, which impedes mixing during the reaction and the subsequent workup. According to EP-A 1,006,127, this problem can be solved by adsorbing the activated polyamino acid onto a solid support. Polyamino acids on a silica gel support are referred to as SCATs (silica adsorbed catalysts).

A further disadvantage of the two-phase conditions is, however, that the use of costly, non-nucleophilic bases (for example, DBU) is necessary in order to make the reaction possible.

According to EP-A 1,006,111, a further variant of the Juliá-Colonna epoxidation is catalysis of the enantioselective epoxidation by the activated polyamino acid in the presence of water, a water-miscible solvent (for example, 1,2-dimethoxyethane), and sodium percarbonate. The use of water-miscible solvents complicates the workup (extraction) in this process.

In the Juliá-Colonna epoxidation, the reaction rate and the enantiomeric excess (ee) that can be achieved depend greatly on the polyamino acid used and the mode of preparation thereof (*Chirality*, 1997, 9, 198–202). In order to obtain approximately comparable results, a standard system with poly-L-leucine (pll) as catalyst and trans-chalcone as precursor is used throughout for the development and description of novel methods in the literature. However, besides D- or L-polyleucine, other poly-amino acids such as, for example, D- or L-neopentylglycine are also used successfully (EP-A 1,006,127).

The object of the present invention was to provide a process that makes the polyamino acid-catalyzed enantioselective epoxidation of α,β-unsaturated enones and α,β-unsaturated sulfones possible but is not subject to the disadvantages of the above-described variants of the Juliá-Colonna epoxidation. It was intended in particular to find a rapid and broadly applicable method that avoids preactivation of the polyamino acid, which must be carried out separately, the use of costly bases and oxidants, and potentially problematic types of reaction procedure and of workup. At the same time, it was intended that the process have advantages in relation to the space/time yield, the handling, economics, and ecology on the industrial scale.

It has now been found, surprisingly, that the epoxidation of α,β-unsaturated enones and α,β-unsaturated sulfones can be carried out with the use of specific phase-transfer catalyst under three-phase conditions with substantially shorter reaction times and, at the same time, even higher enantiomeric excesses.

SUMMARY OF THE INVENTION

The invention thus relates to a process for the epoxidation of α,β-unsaturated enones or α,β-unsaturated sulfones in the presence of (1) a water-soluble base,
(2) an oxidant,
(3) a diastereomer- and enantiomer-enriched homopolyamino acid as catalyst,
(4) water,
(5) an organic solvent that is immiscible or has only limited miscibility with water, and
(6) a phase-transfer catalyst of the formula (I):

$$(R^1R^2R^3R^4A)^+X^- \quad (I)$$

where

A is N or P, $X^-$ is an inorganic or organic anion, $R^1$ and $R^2$ are identical or different and are alkyl, aryl, aralkyl, cycloalkyl, or heteroaryl radicals that are optionally substituted by one or more identical or different halogen radicals, and $R^3$ and $R^4$ are identical or different and are alkyl, aryl, aralkyl, cycloalkyl, or heteroaryl radicals that are optionally substituted by one or more identical or different halogen radicals or $R^3$ and $R^4$ together form a $C_4$–$C_6$-cycloalkyl ring with A, where (i) the total of the carbon atoms and heteroatoms present in the radicals $R^1$, $R^2$, $R^3$, and $R^4$ is at least 13, and (ii) the accessibility q of the phase-transfer catalyst is in the range 0.6 to 1,3, where q is calculated from the following formula:

$$q = \sum_{x=1}^{4}$$

[1/(total of the carbon atoms and heteroatoms in $R^x$)]

DETAILED DESCRIPTION OF THE INVENTION

As an essential feature, the process according to the invention includes the use of specific phase-transfer catalysts.

The variable called the accessibility q is an empirical parameter of a given phase-transfer catalyst of the general formula (I), which has already been described in the literature for tetraalkylammonium salts (*ACS Symp. Ser.*, 1997, 659, 100–102). The phase-transfer catalysts employed in the process according to the invention have an accessibility q in the range 0.6–1.3, preferably in the range 0.7–1.3, and particularly in the range 0.8–1.2.

$X^-$ in the general formula (I) is preferably $F^-$, $Cl^-$, $Br^-$, $I^-$, $OH^-$, $NO_3^-$, $HSO_4^-$, $SO_4^-$, $CH_3COO^-$, $CF_3COO^-$, $C_2H_5COO^-$, $C_3H_7COO^-$, $CF_3SO_3^-$, or $C_4F_9SO_3^-$.

Phase-transfer catalysts of the general formula (I) that have proved suitable are those in which A and $X^-$ have the above-mentioned meanings, $R^1$, $R^2$, $R^3$, and $R^4$ are identical or different and are $C_1$–$C_{18}$-alkyl, $C_6$–$C_{18}$-aryl, $C_7$–$C_{19}$-aralkyl, $C_5$–$C_7$-cycloalkyl, or $C_3$–$C_{18}$-heteroaryl and, at the same time, the above-mentioned conditions (i) and (ii) are met.

Particularly suitable phase-transfer catalysts are $((C_4H_9)_4N)^+Hal^-$, particularly $((C_4H_9)_4N)^+Br^-$, $((C_4H_9)_4P)^+Hal^-$ (particularly $((C_4H_9)_4P)^+Br^-$), or $((C_4H_9)_4N)^+HSO_4^-$.

Phase-transfer catalysts such as Aliquat® 336 ([(CH_3)(C_8H_{17})_3N^+]Cl^-) and Aliquat® 175 ([(CH_3)(C_4H_9)_3N^+]Cl^-), for which accessibility is outside the range of values 0.6 to 1.3, and phase-transfer catalysts such as PEG 400, by contrast, do not lead to the advantages of the process according to the invention. When such catalysts are used, the target products are obtained with only poor enantiomeric excess or poor space-time yield.

The phase-transfer catalysts to be employed according to the invention are normally commercially available or else can be prepared by methods familiar to those skilled in the art.

The amount of added phase-transfer catalyst is not critical and is normally in the range 0.1 to 20 mol % (preferably in the range 0.5 to 15 mol %, and particularly preferably in the range 0.5 to 11 mol %), in each case based on the α,β-unsaturated enones or α,β-unsaturated sulfone employed. However, it is to be observed with amounts which are even lower than 0.1 mol % that the reaction rate decreases markedly, while the high enantiomeric excess is unchanged.

It is possible to employ as α,β-unsaturated enones or α,β-unsaturated sulfones the compounds of the general formula (II):

(II)

in which

X is (C=O) or (SO$_2$), and

R$^5$ and R$^6$ are identical or different and are (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_7$–C$_{19}$)-aralkyl, (C$_1$–C$_{18}$)-heteroaryl, or (C$_2$–C$_{19}$)-heteroaralkyl, each of which radicals is optionally substituted once or more than once by identical or different radicals R$^7$, halogen, NO$_2$, NR$^7$R$^8$, PO$_{0-3}$R$^7$R$^8$, SO$_{0-3}$R$^7$, OR$^7$, CO$_2$R$^7$, CONHR$^7$, or COR$^7$, and where optionally one or more CH$_2$ groups in R$^5$ and R$^6$ are replaced by O, SO$_{0-2}$, NR$^7$, or PO$_{0-2}$R$^7$, where R$^7$ and R$^8$ are identical or different and are H, (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_1$–C$_{18}$)-heteroaryl, (C$_1$–C$_8$)-alkyl-(C$_6$–C$_8$)-aryl, (C$_1$–C$_8$)-alkyl-(C$_1$–C$_{19}$)-heteroaryl, (C$_1$–C$_8$)-alkyl-(C$_3$–C$_8$)-cycloalkyl, each of which radicals is optionally substituted once or more than once by identical or different halogen radicals.

A (C$_1$–C$_{18}$)-alkyl radical means for the purpose of the invention a radical that has 1 to 18 saturated C atoms and that may have branches anywhere. It is possible to include in this group in particular the radicals methyl, ethyl, n-propyl, isopropyl, n-butyl, isobutyl, sec-butyl, tert-butyl, pentyl, and hexyl.

A (C$_2$–C$_{18}$)-alkenyl radical has the features mentioned for the (C$_1$–C$_{18}$)-alkyl radical, with the necessity for at least one carbon-carbon double bond to be present within the radical.

A (C$_2$–C$_{18}$)-alkynyl radical has the features mentioned for the (C$_1$–C$_{18}$)-alkyl radical, with the necessity for at least one carbon-carbon triple bond to be present within the radical.

A (C$_3$–C$_8$)-cycloalky radical means a cyclic alkly radical having 3 to 8 carbon atoms and, where appropriate, a branch anywhere. Included are, particularly, radicals such as cyclopropyl, cyclobutyl, cyclopentyl, cyclohexyl, and cycloheptyl. One or more double bonds may be present in this radical.

A (C$_6$–C$_{18}$)-aryl radical means an aromatic radical having 6 to 18 carbon atoms. Included are, particularly, radicals such as phenyl, naphthyl, anthryl, and phenanthryl.

A (C$_7$–C$_{19}$)-aralkyl radical means a (C$_6$–C$_{18}$)-aryl radical linked via a (C$_1$–C$_8$)-alkyl radical to the molecule.

A (C$_1$–C$_{18}$)-heteroaryl radical designates for the purpose of the invention a five-, six-, or seven-membered aromatic ring system that has 1 to 18 carbon atoms and that has one or more heteroatoms (preferably N, O, or S) in the ring. These heteroaryl radicals include, for example, 2- and 3-furyl, 1-, 2-, and 3-pyrrolyl, 2- and 3-thienyl, 2-, 3-, and 4-pyridyl, 2-, 3-, 4-, 5-, 6-, and 7-indolyl, 3-, 4-, and 5-pyrazolyl, 2-, 4-, and 5-imidazolyl, 1-, 3-, 4-, and 5-triazolyl, 1-, 4-, and 5-tetrazolyl, acridinyl, quinolinyl, phenanthridinyl, 2-, 4-, 5-, and 6-pyrimidinyl, and 4-, 5-, 6-, and 7-(1-aza)-indolizinyl.

A (C$_2$–C$_{19}$)-heteroaralkyl radical means a heteroaromatic system corresponding to the (C$_7$–C$_{19}$)-aralkyl radical.

Halogen or Hal mean in the context of this invention fluorine, chlorine, bromine, and iodine.

The substrates preferably employed in the process according to the invention are preferably α,β-unsaturated enones or α,β-unsaturated sulfones of the general formula (II) in which R$^5$ and R$^6$ are identical or different and are (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl, or (C$_1$–C$_{12}$)-heteroaryl, each of which radicals is optionally substituted once or more than once by identical or different radicals R$^7$, halogen, NO$_2$, NR$^7$R$^8$, PO$_{0-3}$R$^7$R$^8$, or OR$^7$, and R$^7$ and R$^8$ have the meanings indicated above for the general formula (II).

Substrates particularly preferably employed in the process according to the invention are α,β-unsaturated enones or α,β-unsaturated sulfones of the general formula (II) in which R$^5$ and R$^6$ are identical or different and are (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl, or (C$_1$–C$_{12}$)-heteroaryl, each of which radicals is optionally substituted once or more than once by identical or different radicals R$^7$, halogen, NO$_2$, NR$^7$R$^8$, PO$_{0-3}$R$^7$R$^8$, or OR$^7$, and R$^7$ and R$^8$ have the meanings indicated above for the general formula (II), with the proviso that at least one of the radicals R$^5$ or R$^6$ is a (C$_2$–C$_{12}$)-alkenyl, (C$_2$–C$_{12}$)-alkynyl, (C$_6$–C$_{12}$)-aryl-, or (C$_1$–C$_{12}$)-heteroaryl radical.

It is particularly preferred to subject substrates of the general formula (III) to the epoxidation according to the invention:

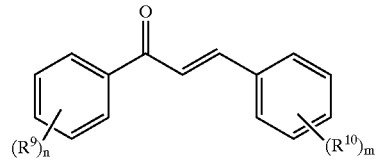

(III)

where n and m are identical or different and are the numbers 0, 1, 2, or 3,

R$^9$ and R$^{10}$ are identical or different and are NR$^7$R$^8$, NO$_2$, OR$^7$, (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl, or (C$_1$–C$_{12}$)-heteroaryl, each of which radicals R$^9$ and R$^{10}$ is optionally substituted once or more than once by identical or different halogen radicals, and R$^7$ and R$^8$ have the meanings mentioned previously for formula (II).

The process according to the invention for preparing the enantiomer-enriched epoxides is carried out in the presence of diastereomer- and enantiomer-enriched homo-polyamino acids as catalyst. It is possible in this connection to use a wide variety of diastereomer- and enantiomer-enriched homo-polyamino acids. Preference is given to the use of homo-polyamino acids selected from the group of polyneopentylglycine, polyleucine, polyisoleucine, polyvaline, polyalanine, and polyphenylalanine. The most preferred from this group are polyneopentylglycine and polyleucine.

The chain length of the polyamino acids will normally be chosen in this connection so that, on the one hand, the chiral induction in the reaction is not impaired and, on the other hand, the costs of synthesizing the polyamino acids are not too great. The chain length of the homo-polyamino acids is preferably in the range from 5 to 100 amino acid repeating units, preferably in the range from 7 to 50 amino acid repeating units. Homo-polyamino acids with 10 to 40 amino acids are very particularly preferred.

The homo-polyamino acids to be employed are not subjected before the epoxidation to any separate preactivation with intermediate isolation nor are they applied to an inorganic support. This increases the economic attractiveness of the process considerably and moreover facilitates industrial implementation.

The homo-polyamino acids can be either employed as such unchanged in the reaction or previously crosslinked with polyfunctional amines or chain-extended by other organic polymers. The crosslinking amines advantageously employed for a crosslinking are diaminoalkanes, preferably 1,3-diaminopropane, or crosslinked hydroxy- or aminopolystyrene (CLAMPS, commercially available). Suitable polymer enlargers are preferably nucleophiles based on polyethylene glycol or polystyrene. Polyamino acids modified in this way are described in *Chem. Commun.*, 1998, 1159–1160, and *Tetrahedron: Asymmetry*, 1997, 8, 3163–3173.

The homo-polyamino acids to be employed in the epoxidation themselves can be prepared by state of the art methods (*J. Org. Chem.*, 1993, 58, 6247–6254, or *Chirality*, 1997, 9, 198–202). The method is to be applied to both optical antipodes of the amino acids. The use of a particular antipode of a polyamino acid correlates with the stereochemistry of the epoxide, that is to say a poly-L-amino acid leads to the optical antipode of the epoxide that is obtained with a poly-D-amino acid.

The amount of the homo-polyamino acid employed is not critical and is normally in the range 0.0001 to 40 mol % (preferably in the range 0.001 to 20 mol %, particularly preferably in the range 0.01 to 15 mol %, and especially in the range 1 to 15 mol %), in each case based on the α,β-unsaturated enone or α,β-unsaturated sulfone employed.

The oxidants used are, as a rule, peroxides, peracids, or inorganic oxidants such as sodium hypochlorite or sodium percarbonate. Peroxides, peracids, or sodium hypochlorite are preferred. An aqueous $H_2O_2$ solution is particularly preferably employed. This aqueous solution may moreover have all the usual concentrations. Further oxidants to be employed in this reaction are the compounds mentioned in *Methoden Org. Chem.* (*Houben-Weyl*), volume 4/1a+b, 59–319, and the compounds mentioned in *Oxidation in Organic Chemistry*, ACS Monograph 186, Washington D.C., 1990, 1–47.

The amount of the oxidant employed may be varied within the wide limits of 1 to 40 equivalents. Surprisingly, and advantageously, the reaction according to the invention still takes place with short reaction times and high enantiomeric excesses even with relatively small amounts of oxidant in the range 1 to 10 equivalents, preferably 1 to 3 equivalents, particularly preferably 1.1 to 2.5 equivalents.

The process according to the invention is carried out in the presence of a water-soluble base. It has proved suitable to employ for this purpose alkali metal hydroxides such as NaOH, KOH, or LiOH. The base is normally employed in the form of an aqueous solution.

The amount of the base employed may be varied within the wide limits of 0.1 to 10 equivalents. Surprisingly, and advantageously, the reaction according to the invention still takes place with short reaction times and high enantiomeric excesses even with relatively small amounts of bases in the range 0.5 to 5 equivalents, preferably 0.8 to 2 equivalents.

The process according to the invention is carried out using a solvent that is immiscible or has only limited miscibility with water. A solvent is regarded as having limited miscibility with water in the context of this invention if a mixture of the organic solvent and water at 20° C. can contain no more than 20% by weight (preferably not more than 10% by weight, and particularly not more than 8% by weight) of water in order to remain a single phase.

Suitable organic solvents are in general unsubstituted or substituted aromatic hydrocarbons, aliphatic hydrocarbons, haloalkanes, and ethers. Particularly suitable are toluene, xylene, hexane, tert-butyl methyl ether, diethyl ether, chloroform, and methylene chloride.

In the optimization of the enantiomeric excess and the reaction rate as a function of the solvent used, similar effects are observed as under conventional three-phase conditions. That is to say, high enantiomeric excesses are obtained, particularly in aromatic hydrocarbons such as toluene, whereas particularly short reaction times are achieved in ethers such as tert-butyl methyl ether or in haloalkanes such as chloroform.

It has furthermore been found that the homo-polyamino acid pll aggregates in tert-butyl methyl ether. Hence tert-butyl methyl ether is an interesting and suitable solvent for a continuous reaction procedure.

The temperature used in the epoxidation is generally in the range from −10 to +50° C., preferably in the range from 0 to +40° C., and particularly at +10 to +30° C.

The pH set during the reaction can be chosen so that an excess of deprotonated $H_2O_2$ is present compared with nondeprotonated $H_2O_2$. On the other hand, the pH in the reaction should not be chosen to be so high as to harm the organic compounds that are employed. The pH is preferably in the range 7 to 14, more preferably in the range 7.5 to 13.

The water content of the system normally results from the fact that, as previously described, individual reaction components of the system, such as the base and the oxidant, are employed in the form of aqueous solutions. The total water content in the reaction mixture is in the range 1 to 70% by weight, preferably in the range 5 to 50% by weight, based on the complete reaction mixture.

In relation to carrying out the reaction, the procedure is normally carried out in such a way that the base, the homo-polyamino acid, the phase-transfer catalyst, the solvent, water, and the substrate are mixed and then the oxidant is added.

The process according to the invention is distinguished by greatly reduced reaction times. Instead of requiring days, epoxidation of the α,β-unsaturated enones and of the α,β-unsaturated sulfones can be achieved with high conversion and high enantioselectivity in only a few hours or even only minutes.

The use according to the invention of the phase-transfer catalyst as cocatalyst permits the necessary amounts of oxidant and of base to be reduced very markedly without having an adverse effect on the reaction rate, conversion, or enantiomeric excess. An additional advantage is that particularly low-cost bases and oxidants can be employed.

Because of the very short reaction times, for the first time hydroxide-sensitive substrates, which cannot be successfully epoxidized by the conventional three-phase conditions (*J. Chem. Soc., Perkin Trans.* 1, 1997, 3501–3507), are also amenable to enantioselective epoxidation under aqueous, three-phase conditions by the process according to the invention.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The process for preparing polyamino acids often provides catalysts for the Juliá-Colonna epoxidation that vary widely in catalytic activity (*Chirality*, 1997, 9, 198–202). The conversion per unit time and the enantiomeric excess can be compared for a particular substrate only if the same polyamino acid batch is used for the epoxidation reaction. For this reason, direct comparison of new results with results published in the literature is impossible, simply because different catalyst batches are inevitably used. For this reason, uniform polyleucine batches were used in each of the subsequent example groups I to VIII (both in the examples according to the invention and in the corresponding comparative examples).

In all the following examples, the conversion and the enantiomeric excess (ee) were determined by methods known from the literature using HPLC on a chiral, nonracemic phase (UV detection).

Example Group I

Examples 1–3 and Comparative Examples CE 4–9
Epoxidation of Trans-Chalcone with Various Phase-Transfer Catalysts The effect of different phase-transfer catalysts (PTC) with different accessibilities on the epoxidation of trans-chalcone (1) to epoxychalcone (2) under three-phase reaction conditions is shown in the following examples.

Scheme 1:

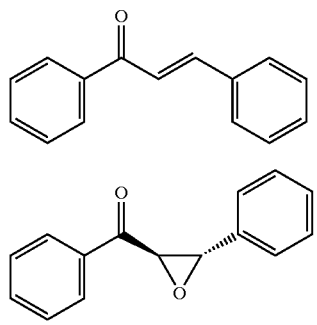

100 mg of non-preactivated polyamino acid pll (11 mol %), 0.24 mmol of trans-chalcone, and 8.5 mg of $(Bu_4N)^+Br^-$ (or 11 mol % of another PTC) were suspended in a mixture of 0.6 ml of toluene and 0.2 ml of NaOH (employed as 5 molar solution, corresponding to 4.2 equivalents). Then 0.7 ml of $H_2O_2$ (employed as 30% strength aqueous solution, corresponding to 28.5 equivalents) was added. This mixture was then allowed to react at room temperature with stirring. After the reaction was complete (or a chosen reaction time), the reaction mixture was diluted with 2 ml of ethyl acetate and then centrifuged. The supernatant was then introduced slowly into a stirred, ice-cold aqueous $NaHSO_3$ solution (4 ml, 20% strength solution). After phase separation, the organic phase was dried over sodium sulfate and concentrated under reduced pressure. The results of this epoxidation are compiled in Table 1 below.

TABLE 1

Effect of PTCs as cocatalysts

| Example | PTC | Reaction time [h] | C# | q | Conversion [%] | ee [%] |
|---|---|---|---|---|---|---|
| 1 | $(Bu_4N)^+Br^-$ | 1.5 | 16 | 1.00 | >99 | 94 |
| 2 | $(Bu_4P)^+Br^-$ | 1.0 | 16 | 1.00 | 91 | 87 |
| 3 | $(Bu_4N)^+HSO_4$ | 1.0 | 16 | 1.00 | 35 | 90 |
| CE 4 | — | 1.5 | — | — | 2 | not determined |
| CE 5 | Aliquat ® 175 = $(MeBu_3N)^+Cl^-$ | 1.0 | 13 | 1.75 | 9 | 77 |

TABLE 1-continued

Effect of PTCs as cocatalysts

| Example | PTC | Reaction time [h] | C# | q | Conversion [%] | ee [%] |
|---|---|---|---|---|---|---|
| CE 6 | PEG 400 | 1.0 | | | 1 | not determined |
| CE 7 | $(Et_3Bn N)^+Cl^-$ | 1.0 | 13 | 1.64 | 0 | not determined |
| CE 8 | Aliquat ® 336 = $(MeOct_3N)^+Cl^-$ | 1.0 | 25 | 1.38 | 71 | 14 |
| CE 9 | $(Oct_4N)^+Br^-$ | 0.5 | 32 | 0.50 | 75 | 7 | q accessibility of the phase-transfer catalyst
C# total of the carbon atoms and heteroatoms in the phase-transfer catalyst employed
Bn benzyl
Me methyl
Et ethyl
Bu n-butyl
Oct n-octyl
PEG polyethylene glycol Example Group II Examples 10–13
Investigation of the Effect of Solvent on the Epoxidation in the Presence of $(Bu_4N)^+Br^-$ as Phase-Transfer Catalyst 100 mg of non-preactivated polyamino acid pll (11 mol %), 0.24 mmol of trans-chalcone, and 8.5 mg of $(Bu_4N)^+Br^-$ (or 11 mol % of another PTC) were suspended in 0.8 ml of the stated solvent and 0.2 ml of NaOH (employed as 5 molar solution, corresponding to 4.2 equivalents). Then 0.7 ml of $H_2O_2$ (employed as 30% strength aqueous solution, corresponding to 28.5 equivalents) was added. This mixture was then allowed to react at room temperature with stirring. After a reaction time of 1 hour, the reaction mixture was diluted with 2 ml of ethyl acetate and then centrifuged. The supernatant was then introduced slowly into a stirred, ice-cold aqueous $NaHSO_3$ solution (4 ml, 20% strength solution). After phase separation, the organic phase was dried over sodium sulfate and concentrated under reduced pressure. The results of these examples are compiled in Table 2 below.

TABLE 2

Effect of the solvent on the epoxidation of trans-chalcone in the presence of $(Bu_4N)^+Br^-$ as PTC

| Example | Solvent | Conversion [%] | ee [%] |
|---|---|---|---|
| 10 | Toluene | 19 | 90 |
| 11 | tert-Butyl methyl ether | 88 | 77 |
| 12 | n-Hexane | 19 | 68 |
| 13 | $CHCl_3$ | 70 | 60 |

Example Group III

Examples 14–17
Epoxidation of Trans-Chalcone in the Presence of Various Quantities of $(Bu_4N)^+Br^-$ as the Phase-Transfer Catalyst 0.27 g of non-preactivated polyamino acid pll (0.3 mol %), 5.0 g of trans-chalcone, and $(Bu_4N)^+Br^-$ in various quantities (see Table 3) were suspended in 20 ml of toluene and 7.2 ml of NaOH (employed as a 5 molar solution, corresponding to 1.5 equivalents). Then 3.7 ml of $H_2O_2$ (employed as a 30% strength aqueous solution, corresponding to 1.5 equivalents) were added. This mixture was then allowed to react at room temperature with stirring. After a reaction time of 2 hours, the reaction mixture was diluted with 50 ml of ethyl acetate and then centrifuged. The supernatant was then introduced slowly into a stirred, ice-cold aqueous NaHSO$_3$ solution (100 ml, 20% strength solution). After phase separation, the organic phase was dried over sodium sulfate and concentrated under reduced pressure. The results of these examples are summarized in Table 3 below.

TABLE 3

Effect of various quantities of phase transfer catalysts on the epoxidation of trans-chalcone

| Example | (Bu$_4$N)$^+$Br$^-$ [g] | (Bu$_4$N)$^+$Br$^-$ [mol %] | Conversion [%] | ee [%] |
|---|---|---|---|---|
| 14 | 0.23 | 3 | 95 | 93 |
| 15 | 0.15 | 2 | 70 | 93 |
| 16 | 0.06 | 0.8 | 49 | 92 |
| 17 | 0.015 | 0.2 | 19 | 94 |

Example Group IV

Example 18 and Comparative Example CE 19
Epoxidation of Trans-Chalcone (1) to Epoxychalcone (2) as Shown in Scheme 1 with NaOCl as Oxidant trans-Chalcone was reacted in the presence of unactivated poly-amino acid pll (11 mol %), 11 mol % (Bu$_4$N)$^+$Br$^-$ (only in Example 18), 6 ml of NaOCl (employed as 7.5% strength aqueous solution), and toluene as solvent at room temperature for 1.5 hours to give the epoxychalcone. Working up took place by dilution with 2 ml of ethyl acetate, centrifugation, subsequent drying over sodium sulfate, and concentration of the supernatant. Table 4 contains the results obtained.

TABLE 4

Epoxidation of trans-chalcone with aqueous NaOCl solution

| Example | PTC | Conversion [%] | ee [%] |
|---|---|---|---|
| 18 | (Bu$_4$N)$^+$Br$^-$ | 32 | 90 |
| CE 19 | — | 1 | not determined |

Example 20
Epoxidation of (E)-1,2-dibenzoylethylene (3) to (4) (Three-Phase Conditions with PTC)

Scheme 2:

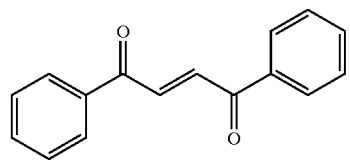

(3)

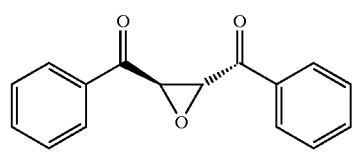

(4)

100 mg of non-preactivated pll (11 mol %), 57 mg of (E)-1,2-dibenzoylethylene, and 8.5 mg of (Bu$_4$N)$^+$Br$^-$ (11 mol %) were suspended in a mixture of 0.8 ml of toluene and 63 μl of NaOH (employed as a 5 molar aqueous solution, corresponding to 1.3 equivalents). Then 32 μl of H$_2$O$_2$ (employed as a 30% strength aqueous solution, corresponding to 1.3 equivalents) were added. This mixture was allowed to react at room temperature with stirring. After a reaction time of 5 min, the reaction mixture was diluted with 2 ml of ethyl acetate and then introduced slowly into a stirred, ice-cold aqueous NaHSO$_3$ solution (4 ml, 20% strength solution). After filtering off the polymer, the organic phase of the filtrate was dried over sodium sulfate and concentrated under reduced pressure. A conversion rate of 100% and an enantiomeric excess of 72% ee were obtained (determined by a shift-$^1$H-NMR experiment with Eu(tfc)$_3$ as a shift reagent).

Example 21
Epoxidation of (E)-1-phenyl-3-(2-pyridinyl)-2-propen-1-one (5) to (6) (three-phase conditions with PTC)

Scheme 3:

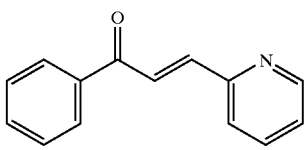

(5)

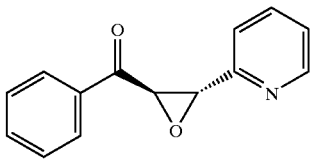

(6)

9 mg of non-preactivated pll (0.5 mol %), 100 mg of (E)-1-phenyl-3-(2-pyridinyl)-2-propen-1-one, and 8.5 mg of (Bu$_4$N)$^+$Br$^-$ (0.3 mol %) were suspended in a mixture of 0.2 ml of toluene and 0.14 ml of NaOH (employed as a 5 molar aqueous solution, corresponding to 1.5 equivalents). Then 74 μl of H$_2$O$_2$ (employed as a 30% strength aqueous solution, corresponding to 1.5 equivalents) were added. This mixture was allowed to react at room temperature with stirring. After a reaction time of 30 min, the reaction mixture was diluted with 2 ml of ethyl acetate and then introduced slowly into a stirred, ice-cold aqueous NaHSO$_3$ solution (4 ml, 20% strength solution). After centrifugation, the supernatant was filtered off and concentrated under reduced pressure. A conversion rate of >99% and an enantiomeric excess of 84% ee were obtained (determined by chiral GC).

In all the following example groups, the process according to the invention was in turn compared with conditions disclosed in the literature, in which no phase-transfer catalyst was added. For this purpose, the best published conditions for the selected exemplary reactions were reproduced with the same polyamino acid batch also employed for carrying out the process according to the invention.

Example Group V

Example 22 and Comparative Examples CE 23–25
Epoxidation of trans-chalcone (1) to epoxychalcone (2) as shown in scheme 1 under three-phase conditions Example 22
3-Phase Conditions with PTC
100 mg of non-preactivated pll, 50 mg of trans-chalcone, and 8.5 mg of (Bu$_4$N)$^+$Br$^-$ were suspended in a mixture of 0.8 ml of toluene and 62 µl of NaOH (employed as 5 molar aqueous solution, corresponding to 1.3 equivalents). Then 32 µl of $H_2O_2$ (employed as 30% strength aqueous solution, corresponding to 1.3 equivalents) were added. This mixture was allowed to react at room temperature with stirring. After a reaction time of 10 min, the reaction mixture was diluted with 2 ml of ethyl acetate and then slowly introduced into a stirred, ice-cold aqueous $NaHSO_3$ solution (4 ml, 20% strength). After centrifugation, the supernatant was dried over sodium sulfate and concentrated under reduced pressure.

Comparative Example CE 23
3-phase Conditions Without PTC 100 mg of non-preactivated pll were suspended in a mixture of 0.8 ml of toluene, 0.2 ml of NaOH (employed as 5 molar aqueous solution, corresponding to 4.2 equivalents), and 0.2 ml of $H_2O_2$ (employed as 30% strength aqueous solution). This mixture was allowed to react at room temperature with stirring for 6 h. Then 50 mg of trans-chalcone and a further 0.5 ml of $H_2O_2$ (employed as 30% strength aqueous solution, corresponding to a total amount of $H_2O_2$ added of 28.5 equivalents) were added. After a reaction time of 1 h, the reaction mixture was diluted with 2 ml of ethyl acetate and then slowly introduced into a stirred, ice-cold aqueous $NaHSO_3$ solution (4 ml, 20% strength). After centrifugation, the supernatant was dried over sodium sulfate and concentrated under reduced pressure.

Comparative Example CE 24
2-phase Conditions without PTC
a) Separate Preactivation of pII 1 g of the polymer was suspended in a mixture of 5 ml of toluene and 10 ml of NaOH (employed as 5 molar aqueous solution) and stirred for 5 days. A gel formed during this time. For workup, the polymer was isolated by decantation, triturated with 20 ml of ethanol, and then filtered off. The filtercake (polymer) was washed with water until neutral. The polymer was then washed three times with acetone and finally dried in vacuo over $P_2O_5$.

b) Epoxidation under 2-phase Conditions 50 mg of trans-chalcone, 25 mg of urea/hydrogen peroxide complex (UHP, 0.26 mmol, 1.1 equivalents), and separately preactivated 94.5 mg of pll (11 mol %, see Section a) for preactivation) were mixed and, after suspending with 2.7 ml of anhydrous THF, 40 µl of DBU (1.1 equivalents) were added. The reaction mixture was allowed to react with stirring at room temperature. After a reaction time of 10 min, the reaction mixture was diluted with 2 ml of ethyl acetate and then centrifuged. The supernatant was then slowly introduced into a stirred, ice-cold aqueous $NaHSO_3$ solution (4 ml, 20% strength). After phase separation, the organic phase was dried over sodium sulfate and concentrated under reduced pressure.

Comparative Example CE 25
SCAT Conditions
a) Preparation of SCAT 1 g of separately preactivated pll (preactivation took place as in Section a) of the method for Comparative Example CE 24) and 3.4 g of silica gel 60 (230–400 mesh, Merck) were mixed, suspended in 30 ml of anhydrous THF, and stirred slowly for 48 h with exclusion of light. The suspension was filtered and the residue was washed twice with 10 ml of anhydrous THF each time. The material (SCAT) was dried in vacuo over $P_2O_5$.

b) Epoxidation under SCAT Conditions 50 mg of trans-chalcone, 25 mg of urea/hydrogen peroxide complex (UHP, 0.26 mmol, 1.1 equivalents), and 419 mg of SCAT (11 mol %) were mixed and, after suspending with 2.7 ml of anhydrous THF, 40 µl of DBU (1.1 equivalents) were added. The reaction mixture was allowed to react with stirring at room temperature. After a reaction time of 10 min, the reaction mixture was filtered. The filtrate was mixed with 2 ml of ethyl acetate and then slowly introduced into a stirred, ice-cold aqueous $NaHSO_3$ solution (4 ml, 20% strength). After phase separation, the organic phase was dried over sodium sulfate and concentrated under reduced pressure.

The results of Example 22 and of Comparative Examples CE 23–25 are compiled in Table 5 below.

TABLE 5

| Example | Conditions | PTC | Reaction time [min] | Conversion [%] | ee [%] |
|---------|-----------|-----|---------------------|----------------|--------|
| 22 | according to the invention | $(Bu_4N)^+Br^-$ | 10 | 97 | 94 |
| CE 23 | 3-phase; not according to the invention | — | 60 | 89 | 94 |
| CE 24 | 2-phase; not according to the invention | — | 10 | 28 | 93 |
| CE 25 | 2-phase, SCAT; not according to the invention | — | 10 | 55 | 95 |

Example Group VI

Example 26 and Comparative Examples CE 27–29
Epoxidation of (E)-1-(2-aminophenyl)-3-phenyl-2-propen-1-one (7) to (8)

Scheme 4:

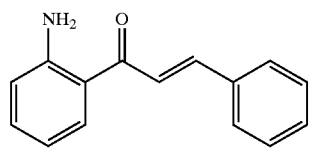

(7)

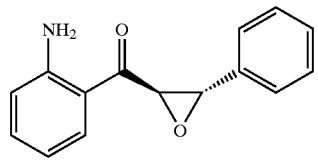

(8)

Example 26
3-phase Conditions with PTC 100 mg of non-preactivated pll, 54 mg of trans-aminochalcone and 8.5 mg of $(Bu_4N)^+Br^-$ were suspended in a mixture of 0.8 ml of toluene and 200 µl of NaOH (employed as 5 molar aqueous solution, corresponding to 4.2 equivalents). Then 125 µl of $H_2O_2$ (employed as 30% strength aqueous solution, corresponding to 5 equivalents) were added. This mixture was allowed to react at room temperature with stirring. After a reaction time of 10 min, the reaction mixture was diluted with 2 ml of ethyl acetate and then centrifuged. The supernatant was then slowly introduced into an ice-cold aqueous $NaHSO_3$ solution (4 ml, 20% strength). After phase separation, the organic phase was dried over sodium sulfate and concentrated under reduced pressure.

Comparative Example CE 27
3-phase Conditions without PTC 100 mg of non-preactivated pII were suspended in a mixture of 0.8 ml of toluene, 0.2 ml of NaOH (employed as 5 molar aqueous solution, corresponding to 4.2 equivalents), and 0.2 ml of $H_2O_2$ (employed as 30% strength aqueous solution). This mixture was allowed to react with stirring for 6 h. Then 54 mg of trans-aminochalcone and a further 0.5 ml of $H_2O_2$ (employed as 30% strength aqueous solution, corresponding to a total amount of $H_2O_2$ added of 28.5 equivalents) were added. After a reaction time of 1 h, the reaction mixture was diluted with 2 ml of ethyl acetate and introduced into a stirred, ice-cold aqueous $NaHSO_3$ solution (4 ml, 20% strength). The mixture was then centrifuged, after which the supernatant was then dried over sodium sulfate and concentrated under reduced pressure.

Comparative Example CE 28
2-phase Conditions a) Separate Preactivation of pII 1 g of the polymer was suspended in a mixture of 5 ml of toluene and 10 ml of NaOH (employed as 5 molar aqueous solution) and stirred for 5 days. A gel formed during this time. For workup, the polymer was isolated by decantation, triturated with 20 ml of ethanol, and then filtered off. The filtercake (polymer) was washed with water until neutral. The polymer was then washed three times with acetone and finally dried in vacuo over $P_2O_5$.

b) Epoxidation under 2-phase Conditions 54 mg of trans-aminochalcone, 25 mg of urea/hydrogen peroxide complex (UHP, 0.26 mmol, 1.1 equivalents), and separately preactivated 94.5 mg of pII (11 mol %, preactivation took place as described in a) above) were mixed and, after suspending with 2.7 ml of anhydrous THF, 40 μl of DBU (1.1 equivalents) were added. The reaction mixture was allowed to react with stirring at room temperature. After a reaction time of 10 min, the reaction mixture was diluted with 2 ml of ethyl acetate and then centrifuged. The supernatant was then slowly introduced into a stirred, ice-cold aqueous $NaHSO_3$ solution (4 ml, 20% strength). After phase separation, the organic phase was dried over sodium sulfate and concentrated under reduced pressure.

Comparative Example CE 29
SCAT Conditions a) Preparation of SCAT 1 g of separately preactivated pII (for method, see Section a) of Comparative Example CE 24) and 3.4 g of silica gel 60 (230–400 mesh, Merck) were mixed, suspended in 30 ml of anhydrous THF, and stirred slowly for 48 h with exclusion of light. The suspension was filtered and the residue was washed twice with 10 ml of anhydrous THF each time. The material (SCAT) was dried in vacuo over $P_2O_5$.

b) Epoxidation under SCAT Conditions 54 mg of trans-aminochalcone, 25 mg of urea/hydrogen peroxide complex (UHP, 0.26 mmol, 1.1 equivalents), and 419 mg of SCAT (11 mol %) were mixed and, after suspending with 2.7 ml of anhydrous THF, 40 μl of DBU (1.1 equivalents) were added. The reaction mixture was allowed to react with stirring at room temperature. After a reaction time of 10 min, the reaction mixture was diluted with 2 ml of ethyl acetate and then centrifuged. The supernatant was slowly introduced into a stirred, ice-cold aqueous $NaHSO_3$ solution (4 ml, 20% strength). After phase separation, the organic phase was dried over sodium sulfate and concentrated under reduced pressure.

The results of Example 26 and of Comparative Examples CE 27–29 are compiled in Table 6 below.

TABLE 6

| Example | Conditions | PTC | Reaction time [min] | Conversion [%] | ee [%] |
|---|---|---|---|---|---|
| 26 | according to the invention | $(Bu_4N)^+Br^-$ | 10 | 58 | 87 |
| CE 27 | 3-phase; not according to the invention | — | 60 | 7 | not determined |
| CE 28 | 2-phase; not according to the invention | — | 10 | 14 | not determined |
| CE 29 | 2-phase, SCAT; not according to the invention | — | 10 | 5 | not determined |

Example Group VII

Example 30 and Comparative Example CE 31
Epoxidation of (E)-1-cyclopropyl-3-phenyl-2-propen-1-one (9) to (10)

Scheme 5:

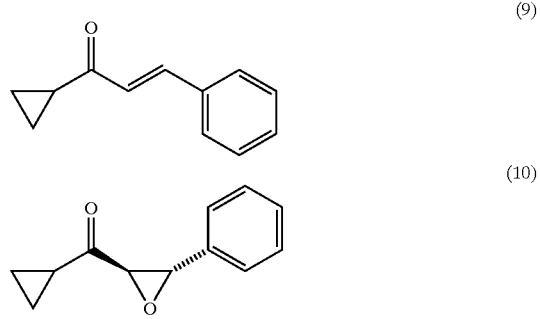

Example 30
3-phase Conditions with PTC 100 mg of non-preactivated pII, 41 mg of (E)-1-cyclopropyl-3-phenyl-2-propen-1-one, and 7.7 mg of $(Bu_4N)^+Br^-$ were suspended in a mixture of 0.8 ml of toluene and 200 μl of NaOH (employed as 5 molar aqueous solution, corresponding to 4.2 equivalents). Then 700 μl of $H_2O_2$ (employed as 30% strength aqueous solution, corresponding to 28.5 equivalents) were added. This mixture was allowed to react with stirring at room temperature. After a reaction time of 5 h, the reaction mixture was diluted with 1 ml of ethyl acetate and then filtered. The organic phase of the filtrate was then slowly introduced into a stirred, ice-cold aqueous $NaHSO_3$ solution (4 ml, 20% strength). After phase separation, the organic phase was dried over sodium sulfate and concentrated under reduced pressure.

Comparative Example CE 31
3-phase Conditions without PTC 100 mg of non-preactivated pII were suspended in a mixture of 0.8 ml of toluene, 0.2 ml of NaOH (employed as 5 molar aqueous solution, corresponding to 4.2 equivalents), and 0.2 ml of $H_2O_2$ (employed as 30% strength aqueous solution). This mixture was allowed to react with stirring at room temperature for 16 h. Then 41 mg of (E)-1-cyclopropyl-3-phenyl-2-propen-1-one and a further 0.5 ml of $H_2O_2$ (employed as 30% strength aqueous solution, corresponding to a total amount of $H_2O_2$ added of 28.5 equivalents) were added. After a reaction time of 5 h, the reaction mixture was diluted with 1 ml of ethyl acetate and then slowly introduced into a stirred, ice-cold aqueous NaHSO₃ solution (4 ml, 20% strength). After filtration, the organic phase of the filtrate was dried over sodium sulfate and concentrated under reduced pressure.

The results of Example 30 and of Comparative Example CE 31 are compiled in Table 7 below

TABLE 7

| Example | Conditions | PTC | Reaction time [h] | Conversion [%] | ee [%] |
|---|---|---|---|---|---|
| 30 | according to the invention | (Bu₄N)⁺Br⁻ | 5 | 40 | 90 |
| CE 31 | 3-phase; not according to the invention | — | 5 | 6 | not determined |

Example Group VIII

Example 32 and Comparative Example CE 33
Epoxidation of Phenyl E-styryl Sulfone (11) to (12)

Scheme 6:

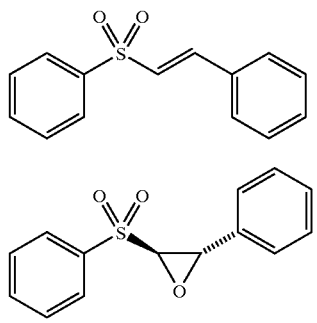

Example 32
3-phase Conditions with PTC 100 mg of non-preactivated pll, 59 mg of phenyl E-styryl sulfone and 8.5 mg of (Bu₄N)⁺Br⁻ were suspended in a mixture of 0.8 ml of toluene and 200 µl of NaOH (employed as 5 molar aqueous solution, corresponding to 4.2 equivalents). Then 125 µl of H₂O₂ (employed as 30% strength aqueous solution, corresponding to 5 equivalents) were added. This mixture was allowed to react at room temperature with stirring. After a reaction time of 2 h, the reaction mixture was diluted with 2 ml of ethyl acetate and then centrifuged. The supernatant was then slowly introduced into 2 ml of water. After phase separation, the organic phase was dried over sodium sulfate and concentrated under reduced pressure.

Comparative Example CE 33
3-phase Conditions with Aliquat® 336 as PTC (accessibility q=1.38)

100 mg of non-preactivated pll, 59 mg of phenyl E-styryl sulfone, and 11 mg of Aliquat® 336 were suspended in a mixture of 0.8 ml of toluene and 200 µl of NaOH (employed as 5 molar aqueous solution, corresponding to 4.2 equivalents). Then 125 µl of H₂O₂ (employed as 30% strength aqueous solution, corresponding to 5 equivalents) were added. This mixture was allowed to react with stirring at room temperature. After a reaction time of 2 h, the reaction mixture was diluted with 2 ml of ethyl acetate and then centrifuged. The supernatant was then slowly introduced into 2 ml of water. After phase separation, the organic phase was dried over sodium sulfate and concentrated under reduced pressure.

The results of Example 32 and of Comparative Example CE 33 are compiled in Table 8 below.

TABLE 8

| Example | Conditions | PTC | Reaction time [h] | Conversion [%] | ee [%] |
|---|---|---|---|---|---|
| 32 | according to the invention | (Bu₄N)⁺Br⁻ | 2 | 79 | 53 |
| CE 33 | not according to the invention | Aliquat ® 336 | 2 | 92 | 22 |

What is claimed is:

1. A process comprising epoxidizing α,β-unsaturated enones or α,β-unsaturated sulfones in the presence of
    (1) a water-soluble base,
    (2) an oxidant,
    (3) a diastereomer- and enantiomer-enriched homopolyamino acid as catalyst,
    (4) water,
    (5) an organic solvent which is immiscible or has only limited miscibility with water, and
    (6) a phase-transfer catalyst of the formula (I):

$$(R^1R^2R^3R^4A)^+X^-$$  (I)

where
      A is N or P,
      X⁻ is an inorganic or organic anion,
      $R^1$ and $R^2$ are identical or different and are alkyl, aryl, aralkyl, cycloalkyl, or heteroaryl radicals that are optionally substituted by one or more identical or different halogen radicals, and
      $R^3$ and $R^4$ are identical or different and are alkyl, aryl, aralkyl, cycloalkyl, or heteroaryl radicals that are optionally substituted by one or more identical or different halogen radicals or $R^3$ and $R^4$ together form a $C_4$–$C_6$-cycloalkyl ring with A,
    where
      (i) the total of the carbon atoms and heteroatoms present in the radicals $R^1$, $R^2$, $R^3$, and $R^4$ is at least 13, and
      (ii) the accessibility q of the phase-transfer catalyst is in the range 0.6 to 1.3, where q is calculated from the following formula:

$$q = \sum_{x=1}^{4} [1/(\text{total of the carbon atoms and heteroatoms in } R^x)].$$

2. A process according to claim 1 wherein the phase-transfer catalyst has an accessibility q in the range 0.7 to 1.3.

3. A process according to claim 1 wherein X in the formula (I) is F⁻, Cl⁻, Br⁻, I⁻, OH⁻, NO₃⁻, HSO₄⁻, SO₄⁻, CH₃COO⁻, CF₃COO⁻, C₂H₅COO⁻, C₃H₇COO⁻, CF₃SO₃⁻, or C₄F₉SO₃⁻.

4. A process according to one claim 1 wherein, for the phase-transfer catalysts of the formula (I), $R^1$, $R^2$, $R^3$, and $R^4$ are identical or different and are C₁–C₁₈-alkyl, C₆–C₁₈-aryl, C₇–C₁₉-aralkyl, C₅–C₇-cycloalkyl, or C₃–C₁₈-heteroaryl.

5. A process according to claim 1 wherein the phase-transfer catalyst is $((C_4H_9)_4N)^+Hal^-$, $((C_4H_9)_4P)^+Hal^-$, or $((C_4H_9)_4N)^+HSO_4^-$.

6. A process according to claim 1 wherein the phase-transfer catalyst is employed in an amount in the range 0.1 to 20 mol %, based on the α,β-unsaturated enone or α,β-unsaturated sulfone.

7. A process according to claim 1 wherein the α,β-unsaturated enones or α,β-unsaturated sulfones have the formula (II):

$$R^5 \diagdown X \diagdown R^6 \quad (II)$$

in which

X is (C=O) or (SO$_2$), and

R$^5$ and R$^6$ are identical or different and are (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_7$–C$_{19}$)-aralkyl, (C$_1$–C$_{18}$)-heteroaryl or (C$_2$–C$_{19}$)-heteroaralkyl, each of which radicals is optionally substituted once or more than once by identical or different radicals R$^7$, halogen, NO$_2$, NR$^7$R$^8$, PO$_{0-3}$R$^7$R$^8$, SO$_{0-3}$R$^7$, OR$^7$, CO$_2$R$^7$, CONHR$^7$, or COR$^7$, and where optionally one or more CH$_2$ groups in R$^5$ and R$^6$ are replaced by O, SO$_{0-2}$, NR$^7$, or PO$_{0-2}$R$^7$, where R$^7$ and R$^8$ are identical or different and are H, (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_1$–C$_{18}$)-heteroaryl, (C$_1$–C$_8$)-alkyl-(C$_6$–C$_8$)-aryl, (C$_1$–C$_8$)-alkyl-(C$_1$–C$_{18}$)-heteroaryl, (C$_1$–C$_8$)-alkyl-(C$_3$–C$_8$)-cycloalkyl, each of which radicals is optionally substituted once or more than once by identical or different halogen radicals.

8. A process according to claim 1 wherein the α,β-unsaturated enones or α,β-unsaturated sulfones have the formula (II):

$$R^5 \diagdown X \diagdown R^6 \quad (II)$$

in which

X is (C=O) or (SO$_2$),

R$^5$ and R$^6$ are identical or different and are (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl or (C$_1$–C$_{12}$)-heteroaryl, each of which radicals is optionally substituted once or more than once by identical or different radicals R$^7$, halogen, NO$_2$, NR$^7$R$^8$, PO$_{0-3}$R$^7$R$^8$, or OR$^7$, and R$^7$ and R$^8$ are identical or different and are H, (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_1$–C$_{18}$)-heteroaryl, (C$_1$–C$_8$)-alkyl-(C$_6$–C$_8$)-aryl, (C$_1$–C$_8$)-alkyl-(C$_1$–C$_{18}$)-heteroaryl, (C$_1$–C$_8$)-alkyl-(C$_3$–C$_8$)-cycloalkyl, each of which radicals is optionally substituted once or more than once by identical or different halogen radicals.

9. A process according to claim 1 wherein the substrates employed in the process according to the invention are α,β-unsaturated enones or α,β-unsaturated sulfones of the formula (II):

$$R^5 \diagdown X \diagdown R^6 \quad (II)$$

in which

X is (C=O) or (SO$_2$),

R$^5$ and R$^6$ are identical or different and are (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl or (C$_1$–C$_{12}$)-heteroaryl, each of which radicals is optionally substituted once or more than once by identical or different radicals R$^7$, halogen, NO$_2$, NR$^7$R$^8$, PO$_{0-3}$R$^7$R$^8$ or OR$^7$, and R$^7$ and R$^8$ are identical or different and are H, (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_1$–C$_{18}$)-heteroaryl, (C$_1$–C$_8$)-alkyl-(C$_6$–C$_8$)-aryl, (C$_1$–C$_8$)-alkyl-(C$_1$–C$_{18}$)-heteroaryl, (C$_1$–C$_8$)-alkyl-(C$_3$–C$_8$)-cycloalkyl, each of which radicals is optionally substituted once or more than once by identical or different halogen radicals, with the proviso that at least one of the radicals R$^5$ or R$^6$ is a (C$_2$–C$_{12}$)-alkenyl, (C$_2$–C$_{12}$)-alkynyl, (C$_6$–C$_{12}$)-aryl-, or (C$_1$–C$_{12}$)-heteroaryl radical.

10. A process according to claim 1 wherein the substrates employed in the process according to the invention are compounds of the formula (III):

$$(III)$$

where n and m are identical or different and are the numbers 0, 1, 2, or 3,

R$^9$ and R$^{10}$ are identical or different and are NR$^7$R$^8$, NO$_2$, OR$^7$, (C$_1$–C$_{12}$)-alkyl, (C$_2$–C$_{12}$)-alkenyl, (C$_2$–C$_{12}$)-alkynyl, (C$_5$–C$_8$)-cycloalkyl, (C$_6$–C$_{12}$)-aryl, or (C$_1$–C$_{12}$)-heteroaryl, each of which radicals R$^9$ and R$^{10}$ is optionally substituted once or more than once by identical or different halogen radicals, and R$^7$ and R$^8$ are identical or different and are H, (C$_1$–C$_{18}$)-alkyl, (C$_2$–C$_{18}$)-alkenyl, (C$_2$–C$_{18}$)-alkynyl, (C$_3$–C$_8$)-cycloalkyl, (C$_6$–C$_{18}$)-aryl, (C$_1$–C$_{18}$)-heteroaryl, (C$_1$–C$_8$)-alkyl-(C$_6$–C$_8$)-aryl, (C$_1$–C$_8$)-alkyl-(C$_1$–C$_{18}$)-heteroaryl, (C$_1$–C$_8$)-alkyl-(C$_3$–C$_8$)-cycloalkyl, each of which radicals is optionally substituted once or more than once by identical or different halogen radicals.

11. A process according to claim 1 wherein the diastereomer- and enantiomer-enriched homo-polyamino acids are selected from the group of polyneopentylglycine, polyleucine, polyisoleucine, polyvaline, polyalanine, and polyphenylalanine.

12. A process according to claim 1 wherein the polyamino acid has a chain length in the range from 5 to 100 amino acid repeating units.

13. A process according to claim 1 wherein the homopolyamino acids are not subjected before their use as catalyst of the epoxidation to a separate preactivation with intermediate isolation and are not applied to an inorganic support.

14. A process according to claim 1 wherein the homopolyamino acids are employed in the range 0.0001 to 40 mol %, based on the α,β-unsaturated enone or α,β-unsaturated sulfone.

15. A process according to claim 1 wherein the oxidant is a peroxide, peracid, or inorganic oxidant.

16. A process according to claim 1 wherein the oxidant is an aqueous $H_2O_2$ solution.

17. A process according to claim 1 wherein 1 to 40 equivalents of the oxidant is employed.

18. A process according to claim 1 wherein the water-soluble base is an alkali metal hydroxide.

19. A process according to claim 1 wherein 0.1 to 10 equivalents of the base is employed.

20. A process according to claim 1 wherein the organic solvent is an unsubstituted or substituted aromatic hydrocarbon, aliphatic hydrocarbon, haloalkane, or ether.

21. A process according to claim 1 wherein the reaction temperature is in the range from −10 to +50° C.

* * * * *